United States Patent [19]

Carpenter et al.

[11] 4,146,735
[45] Mar. 27, 1979

[54] PREPARATION OF α,β-UNSATURATED CARBOXYLIC ACIDS VIA MANNICH INTERMEDIATES

[75] Inventors: Clark R. Carpenter, Berlin, N.J.; James S. Clovis, Mougins, France

[73] Assignee: Rohm and Haas Company, Philadelphia, Pa.

[21] Appl. No.: 797,091

[22] Filed: May 16, 1977

[51] Int. Cl.² .................... C07C 51/00; C07C 57/02; C07C 57/04
[52] U.S. Cl. .................................... 562/599; 204/79; 260/584 A; 260/593 R; 260/601 R; 562/405; 562/418; 562/421; 562/507; 562/510; 562/526; 562/532; 562/600
[58] Field of Search ............ 260/514 J, 514 L, 526 N, 260/530 R, 515 R, 584 A; 204/79; 562/599, 526, 600

[56] References Cited

FOREIGN PATENT DOCUMENTS 37-1713  5/1962  Japan ................... 260/526 N

*Primary Examiner*—Vivian Garner
*Attorney, Agent, or Firm*—Jordan J. Driks

[57] ABSTRACT

A process for the preparation of a α,β-unsaturated carboxylic acid by reacting formaldehyde, another aldehyde and a mineral acid salt of a secondary amine to form an intermediate Mannich base salt; oxidizing the Mannich base salt to the corresponding aminoacid salt; thermally cracking the aminoacid salt to yield an aqueous reaction products mixture of an α,β-unsaturated carboxylic acid and the mineral acid salt of the secondary amine; and separating and isolating the aqueous reaction products.

11 Claims, No Drawings

PREPARATION OF α,β-UNSATURATED CARBOXYLIC ACIDS VIA MANNICH INTERMEDIATES

This invention relates to the preparation of α,β-unsaturated carboxylic acids by the oxidation of Mannich base salts and thermal cracking of the oxidation product.

One method for the production of α,β-unsaturated carboxylic acids, such as acrylic and methacrylic acid, is by the catalytic oxidation of the appropriate unsaturated aldehyde, such as acrolein and methacrolein, respectively. These precursor unsaturated aldehydes can be prepared in a number of ways, one of which involves the reaction of formaldehyde, another aldehyde and the salt of a secondary amine. This reaction gives rise to a Mannich base salt, which is a kind of protected aldehyde that can be decomposed to yield the corresponding unsaturated aldehyde and the amine salt. An entire sequence for the preparation of an α,β-unsaturated carboxylic acid then would entail the condensation reaction to produce the Mannich base salt, decomposition of this salt to obtain the unsaturated aldehyde, and finally the oxidation of the aldehyde to the corresponding α,β-unsaturated acid.

However, the need to recover the unsaturated aldehyde from the aqueous decomposition reaction mixture prior to oxidation to the corresponding acid is a disadvantage, since this not only adds an additional step in the overall unsaturated carboxylic acid process, but also gives rise to decreased acid yield through aldehyde losses experienced during the aldehyde recovery process. Such losses, although not significant in isolated cases, are very significant because their effect is cumulative in large-scale continuous processes. Moreover, the double bond of such unsaturated aldehydes is extremely reactive, and oxidation of these aldehydes, when the double bond is unprotected, gives low yield because of enhanced polymer and by-product formation. It has now been found, however, that all these disadvantages can be readily overcome by the process of this invention.

It has been found that α,β-unsaturated carboxylic acids can be prepared by reacting formaldehyde, another aldehyde and a secondary amine mineral salt to form an intermediate Mannich base salt; oxidizing the intermediate base salt to the corresponding aminoacid salt; thermally cracking the aminoacid salt to yield an aqueous reaction products mixture of an α,β-unsaturated carboxylic acid and the secondary-amine acid salt; and separating and isolating the products of the cracking step.

This process proceeds according to the following equations, which illustrate the preparation of methacrylic acid from formaldehyde, propionaldehyde and dimethylamine hydrochloride:

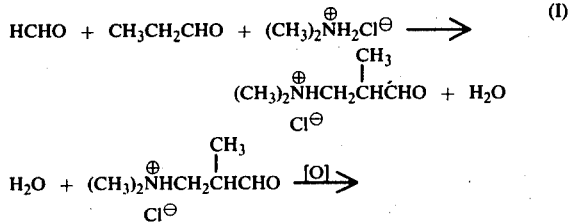

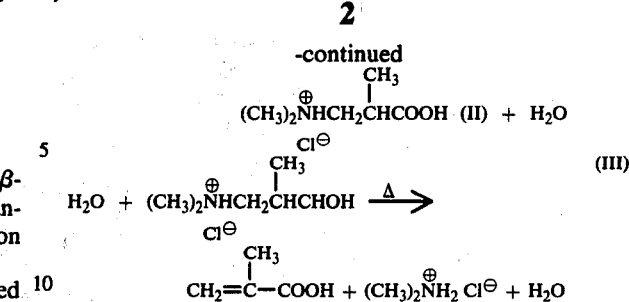

The first step in the process, illustrated by Equation I, is a condensation reaction between formaldehyde, another aldehyde and a secondary amine mineral acid salt which yields a Mannich base salt. In Equation I, this Mannich base salt is postulated to be dimethylaminoisobutyraldehyde hydrochloride. The reaction is carried out at a temperature in a range of from about 25° to about 60° C. and at a pH in the range of from about 3.5 to about 7.6. In optimum cases, the pH is about 5.5 and the temperature about 30° C. Best results are obtained when formaldehyde and the other aldehyde are employed in equimolecular proportions and the proportion of the secondary amine salt is in excess of the stoichiometric ratio. Preferably, from about 2 to about 5 moles of amine salt are used per mole of either aldehyde.

The aldehydes useful in the reaction are any aldehydes higher than formaldehyde, including the aliphatic, cyclic, aromatic and heterocyclic aldehydes. Most preferred are those in which the alpha carbon atom attached to the carbonyl group is also directly attached to two hydrogen atoms and to another carbon atom, for example to a carbon atom of an alkyl group such as in acetaldehyde, propionaldehyde, butyraldehyde, valeraldehyde, and the like. The secondary amine salts useful in the process are the salts of dialkylamines, such as the salts of dimethylamine, diethylamine, diisopropylamine and the like, as well as the salts of piperdine, morpholine, and the like. The mineral acids used to form the salts are such acids as hydrochloride, sulfuric, phosphoric, and the like. The most preferred secondary amine salt is dimethylamine hydrochloride.

The second step of the process is the oxidation of the intermediate Mannich base salt to an aminoacid salt. This oxidation is illustrated in Equation II, where the postulated dimethylaminoisobutyraldehyde hydrochloride is oxidized to β-dimethylaminoisobutyric acid hydrochloride.

This oxidation can be accomplished in a number of ways. An autoxidation method is attractive since stoichiometric amounts of an oxidizing agent are not necessary. Under such a scheme, the Mannich base salt is oxidized by air or oxygen in the presence of a catalytic agent. It has been found that cobaltous ion and hydrogen peroxide can initiate a free radical oxidation of the intermediate Mannich base salt to yield the corresponding amino acid salt. Such an autoxidation proceeds best at a pH in the range of from about 1.0 to about 2.0 and at temperatures of about 30° to 50° C. Other free radical oxidation initiators include iron, nickel, copper, manganese, and the like.

In addition to autoxidation, the intermediate Mannich base salt can be oxidized in high yields to the corresponding aminoacid salt by use of conventional oxidizing agents. Typically useful in this regard are hydrogen peroxide, or hydrogen peroxide promoted by selenium dioxide, peracetic acid, acidic potassium chromate, acidic potassium permanganate, Benedict's reagent (cupric oxide-sodium citrate complex in aqueous sodium carbonate solution) and the like. The oxidations are carried out at a pH in the range from about 0.3 to about 4.0 and preferably from about 1.0 to 1.5 and at temperatures in the range of from about 30° to about 70° C. The conversions using such oxidizing agents range from 26% to 90% with selectivities ranging from 30% to 90%. The preferred oxidizing agent is hydrogen peroxide, and the most preferred is an oxidizing system of hydrogen peroxide promoted by selenium dioxide.

It is also possible to effect the oxidation by electrosynthetic means. Thus, anodic oxidation of the Mannich base salt is possible, especially in light of the fact that the salt is present in an aqueous solution, which avoids the common organic electrosynthesis problem of solubilizing organic compounds in water so as to bring about contact between the organic compounds and the electrodes.

The thermal cracking of the aminoacid salt to the desired $\alpha,\beta$-unsaturated carboxylic acid and the secondary amine salt, is carried out either in the liquid phase or vapor phase. The liquid phase and vapor phase cracking are both pH dependent, with significant conversions occurring in the 1.0 and 6.0 pH range. This pH dependence exists for all cracking temperatures, which are about 175° to 275° C. (e.g., about 175°-225° C.) and about 175° to 250° C. for the liquid and vapor phases, respectively. In both cases, it is desirable to carry out the cracking under an inert atmosphere, such as nitrogen. The cracking yields the desired $\alpha,\beta$-unsaturated carboxylic acid and the originally used secondary amine salt. Under the pH and temperature parameters outlined, it is possible to obtain desired carboxylic acids in > 90% yield in either liquid or vapor phase. The cracking step yields an aqueous reaction products mixture from which it is necessary to extract the desired product $\alpha,\beta$-unsaturated carboxylic acid. Any method of separating and isolating the product acid from the aqueous reaction mixture is suitable. However, solvent extraction is preferable, because a clean separation can be made with a minimum of product loss, such as occurs in separation by distillation due to polymerization of the product. Most preferably, the extraction solvent has a high selectivity for the product acid, a low selectivity for the amine salt, and carries a reasonably low amount of water into the extract layer. In the case of the preparation of methacrylic acid by the process of the invention, methyl methacrylate is an excellent solvent for methacrylic acid, in that > 98% product acid is extracted and 96-100% of the amine salt is left in the water phase. With such high efficiency, it is possible to run the process continuously, isolating product acid and recycling the aqueous amine salt solution to the initial condensation range. The extracted product is separated from extracting solvent and is purified by conventional techniques.

The following examples are given to illustrate the invention without limiting the same.

EXAMPLE 1

A 3-liter flask is equipped with a mechanical stirrer, condenser, three addition funnels, a pH probe and a thermometer. The flask is charged with 700 g. of water and 0.5 g. of hydroquinone. One addition funnel contains 1482.6 g. of 39% aqueous dimethylamine hydrochloride, the second contains a mixture of 567.7 g. of 37% aqueous formaldehyde plus 414.8 g. of propionaldehyde and the third contains some 10% aqueous dimethylamine solution for pH regulations. The amine hydrochloride and aldehyde mixture are metered into the stirred reactor over a 2 hour period at equivalent rates and the total contents stirred an additional 2 hours. The temperature is maintained at 30° C. by cooling and the pH is kept at 5.5-5.6 by addition of small amounts of dimethylamine. After the reaction is complete the pH is reduced, by addition of aqueous 5% hydrochloric acid, to 2.0.

The mixture is extracted three times with 100 g. portions of di-n-butyl ether to remove a total of 17 g. of unreacted propionaldehyde and methacrolein formed by degradation of the desired intermediate. GLC and differential non-aqueous titration analysis of the 3.22 g. of raffinate indicates that the Mannich intermediate ($\alpha$-dimethylaminoisobutyraldehyde hydrochloride) is present in 25% concentration, the yield of product amounts to 82%. The yield of methacrolein is 3% and unconverted propionaldehyde amounts to 4%.

EXAMPLE 2

Using the reactor of Example 1, a mixture of 406 g. propionaldehyde (7.0 moles) and 568 g. of 37% aqueous formaldehyde (7.0 moles pure $CH_2O$ is added to a stirred solution of 1273 g. 44.8% aqueous dimethylamine hydrochloride solution (7.0 moles pure dimethylamine hydrochloride) at 30° C. over a 30 minute period. A pH drop of 4.3 to 3.5 occurs. At the end of the addition, 8.0 g. 40% aqueous dimethylamine is added to raise the pH to 5.5. The solution is then stirred for 4½ hours at 40° C. until the reaction exotherm dies off.

The solution is extracted two times with 500 c.c. portions of diethyl ether to remove aldehyde and the raffinate is acidified to pH 1.9 using concentrated hydrochloric acid. Analysis indicates that a 92% yield of Mannich base salt intermediate is obtained.

EXAMPLE 3

A mixture of 60 ml. 25% aqueous Mannich Intermediate and 0.75 gm. cobaltous acetate tetrahydrate in 90 ml. water is charged to a countercurrent tower reactor. The solution of pH 1.4, is circulated downward at 150 c.c./hr. against an opposing current of oxygen at 50 c.c./min. Temperature is maintained at 50° C. over the 1½ hour reaction period. At the end of this time it is found that 49% of the Mannich intermediate of Example 1 is converted with a selectivity of 41% to $\beta$-dimethylaminoisobutyric acid hydrochloride. Small amounts of acetone and higher molecular weight material are also formed.

EXAMPLE 4

In the Example, hydrogen peroxide is used to promote the autoxidation. A 2.0 mole ratio of Mannich intermediate/$H_2O_2$, catalyzed by cobaltous acetate tetrahydrate is reacted to 30° to 70° C. and at an initial pH of 1.1. After 4 hours at 50° C. and at a pH of 1.3, the reaction becomes exothermic with the temperature increasing to 76° C. and with oxygen being taken up. At the end of this exotherm, 53% of the Mannich intermediate is converted with a selectivity of 72%

EXAMPLE 5

A 250 ml. flask is equipped with a magnetic stirrer, a pH probe, a condensing system, a sintered glass gas inlet tube under the liquid surface level and a port to admit hydrogen peroxide. 150 g. of the Mannich intermediate solution obtained in Example 2 is charged to the system and oxygen is admitted through the gas tube at 95 ml./min. A 30% hydrogen peroxide solution is continuously pumped to the reactor at 7.4 g./hr. Reaction time is 6 hours, with temperatures being increased from 30° to 70° C. throughout the period and pH varying 1.2–2.2. The intermediate is 85% converted to the desired β-dimethylaminoisobutyric acid hydrochloride with a 61% selectivity.

EXAMPLE 6

The experiment of Example 5 is repeated, except that the $H_2O_2$ feed rate is 8.3 gm./hr. and 5.6 gm. of selenium dioxide is added to the reactor. The conversion is 57% with a 90% selectivity.

EXAMPLE 7

A 50% solution of Mannich intermediate solution (total of 150 g.) obtained in Example 2 and 50 g. of potassium dichromate are charged to a 500 ml. reactor. Concentrated sulfuric acid is then added over a 1 hour period keeping the stirred solution at or below 30° C. The reactants are then heated to 50° C. over a 3 hour period and held an additional 2 hours at this temperature. GLC and differential non-aqueous titration analysis of the solution, after filtration to remove insoluble sulfate, indicates that the Mannich intermediate is converted to β-dimethylaminoisobutyric acid hydrochloride to the extent of 68% with a selectivity of 72%.

EXAMPLE 8

375 g. of water, 107 g. of concentrated sulfuric acid and 150 g. of 50% aqueous Mannich intermediate obtained in Example 2 are charged to a reactor in the order listed at a temperature of 15° C. A total of 53 g. of potassium permanganate is then added in 5 g. amounts to the stirred solution at a temperature of 20° C. After the permanganate addition is complete, the temperature is increased to 50° C. over a 3 hour period and held there for an additional 2 hours. The precipitated manganese dioxide is removed, and analysis of the solution shows 39% conversion to the desired β-dimethylaminoisobutyric acid hydrochloride in 52% selectivity.

EXAMPLE 9

An aqueous 25% solution of β-dimethylisobutyric acid hydrochloride, at pH 1.9, is heated for 4 minutes at 225° C. in a sealed pressure tube. Analysis of the resulting solution indicates that an 87% yield of methacrylic acid is obtained.

EXAMPLE 10

A 33.3% solution of β-dimethylaminoisobutyric acid hydrochloride in water at pH 1.0 is pumped at 26.5 g./hr. through a 290 c.c. volume reactor filled with glass beads heated to 188° C. Nitrogen flowing at 50 ml./min. is employed as a diluent carrier, and contct time of the reactant is 34.5 seconds under these conditions. Analysis of the reactor effluent indicates that methacrylic acid is formed in 92% yield.

EXAMPLE 11

A thermal cracking reactant mixture of 12% methacrylic acid, 11% dimethylamine hydrochloride and 77% water is subjected to methyl methacrylate extraction. Different volumetric ratios of the solvent methyl methacrylate and the mixtures are shaken in separating funnels. After shaking, the mixtures are allowed to settle into two layers, the layers separated and then analyzed for component composition. The results are shown in Table I. Dimethylaminoisobutyric acid, a minor component (~0.2%), is not included in this analysis.

TABLE I

| Solvent/Solute, by volume | Extract, % | | | | Distribution Data Raffinate, % | | | | % Recovery in Extract | | % Recovery in Raffinate |
|---|---|---|---|---|---|---|---|---|---|---|---|
| | MMA[1] | MMA[2] | $H_2O$ | DMA[3] HCl | MMA | MAA | $H_2O$ | DMA HCl | MMA | MAA | DMA . HCl |
| 1:7 | 55.2 | 38.4 | 7.2 | trace | 0.48 | 3.4 | 85.2 | 12.2 | 96.8 | 75 | 98.7 |
| 1:3 | 71.7 | 24.4 | 5.1 | 0 | 0.66 | 2.1 | 85.1 | 12.7 | 98.1 | 85 | 100.5 |
| 1:1 | 86.4 | 10.9 | 3.0 | 0 | 0.78 | 1.1 | 83.7 | 12.85 | 99.3 | 92.5 | 100.0 |
| 3:1 | 94.4 | 4.2 | 2.0 | trace | 0.76 | 0.45 | 86.2 | 13.1 | 99.8 | 97.2 | 96.7 |
| 7:1 | 97.5 | 1.4 | 1.5 | trace | 0.80 | 0.24 | 84.6 | 13.7 | 99.7 | 98.0 | 97.0 |

[1]MMA = Methyl methacrylate
[2]MAA = Methacrylic acid
[3]DMA . HCl = Dimethylamine hydrochloride

We claim:
1. A process for the preparation of α,β-unsaturated carboxylic acids which comprises the steps of:
   (a) reacting, at a temperature of from about 25° C. to about 60° C. and a pH of from about 3.5 to about 7.6, formaldehyde, another aldehyde selected from the class consisting of acetaldehyde, propionaldehyde, butyraldehyde and valeraldehyde, and a secondary amine mineral acid salt to form an intermediate Mannich base salt;
   (b) Oxidizing said intermediate Mannich base salt at a pH of from about 0.3 to about 4.0 and a temperature of from about 30° C. to about 70° C. to the corresponding aminoacid salt;
   (c) thermally cracking the aminoacid salt formed in step (b) at a pH of from about 1.0 to about 6.0 and a temperature of from about 175° C. to about 275° C. to yield an aqueous reaction products mixture of an α,β-unsaturated carboxylic acid and the secondary amine mineral acid salt; and
   (d) separating and isolating the products of step c).
2. The process of claim 1, where the aminoacid salt is obtained by catalytic autoxidation of the Mannich base salt.
3. The process of claim 2, where the catalyst is a cobaltous salt.
4. The process of claim 1 wherein step b) is carried out in the presence of an oxidizing agent selected from hydrogen peroxide, acidic potassium chromate, acidic potassium permanganate and peracetic acid.
5. The process of claim 1 wherein step b) is carried out in the presence of an oxidizing agent which is hydrogen peroxide.
6. The process of claim 5, where the hydrogen peroxide is promoted with selenium dioxide.

7. The process of claim 1, where the aminoacid salt is cracked in the liquid phase at a temperature of about 175° to 225° C. and at a pH of about 1.0 to 6.0.

8. The process of claim 1, where the aminoacid salt is cracked in the vapor phase at a temperature of about 175° to 250° C. and at a pH of about 1.0 to 6.0.

9. The process of claim 1, where the secondary amine mineral acid salt recovered in step (d) is recycled to step (a).

10. The process of claim 1, where the aldehyde is propionaldehyde, the secondary amine mineral acid salt is diemthylamine hydrochloride and the $\alpha,\beta$-unsaturated carboxylic acid is methacrylic acid.

11. The process of claim 10, where the product methacrylic acid is recovered by extraction from the products mixture with methyl methacrylate.

* * * * *

UNITED STATES PATENT AND TRADEMARK OFFICE
CERTIFICATE OF CORRECTION

PATENT NO. : 4,146,735
DATED : March 27, 1979
INVENTOR(S) : Carpenter et al.

It is certified that error appears in the above-identified patent and that said Letters Patent are hereby corrected as shown below:

Col. 2, line 6 - CHCHOH - should read -- CHCOOH --

Col. 4., line 18 ( $\alpha$- should read -- $\beta$- --

Col. 8, line 6 - diemthylamine - should read -- dimethylamine --

Signed and Sealed this

Twenty-third Day of October 1979

[SEAL]

Attest:

RUTH C. MASON
Attesting Officer

LUTRELLE F. PARKER
Acting Commissioner of Patents and Trademarks